(12) United States Patent
Bunker et al.

(10) Patent No.: US 7,651,261 B2
(45) Date of Patent: Jan. 26, 2010

(54) SYSTEM AND METHOD FOR THERMAL INSPECTION OF PARTS

(75) Inventors: Ronald Scott Bunker, Niskayuna, NY (US); Jason Randolph Allen, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 201 days.

(21) Appl. No.: 11/775,502

(22) Filed: Jul. 10, 2007

(65) Prior Publication Data
US 2009/0016402 A1 Jan. 15, 2009

(51) Int. Cl.
*G01N 25/18* (2006.01)
(52) U.S. Cl. ....................................... 374/43
(58) Field of Classification Search ................ 374/107, 374/43
See application file for complete search history.

(56) References Cited

U.S. PATENT DOCUMENTS

| | | | |
|---|---|---|---|
| 4,067,237 A | 1/1978 | Arcella | |
| 4,621,929 A | 11/1986 | Phillips | |
| 4,644,162 A | 2/1987 | Bantel et al. | |
| 4,777,368 A | 10/1988 | Kerlin, Jr. | |
| 4,896,281 A | 1/1990 | Mack | |
| 5,111,046 A | 5/1992 | Bantel | |
| 6,422,743 B1 | 7/2002 | Nirmalan et al. | |
| 6,585,408 B2 | 7/2003 | El-Gabry et al. | |
| 6,732,582 B2 | 5/2004 | Bunker et al. | |
| 6,804,622 B2 | 10/2004 | Bunker et al. | |
| 7,440,820 B2 * | 10/2008 | Gougerot et al. | 700/278 |
| 2002/0011852 A1 | 1/2002 | Mandelis et al. | |

FOREIGN PATENT DOCUMENTS

JP 1201165 8/1989

OTHER PUBLICATIONS

A. Daniels, "Non-destructive Pulsed Infared Quantitative Evaluation of Metals," Thermosense XVIII: An International Conference on Thermal Sensing and Imaging Diagnostic Applications, Apr. 10-12, 1996, Orlando, Florida, vol. 2766, pp. 185-201.
"Thermography Inspection System for Gas Turbine Blades," 7th ECNDT, Copenhagen, May 1998, 8 pages.
J. Stiglich, Jr., et al., "The Thermal Inertia Analysis Technique in Gas Turbine Component Reliability Assessment," Oct. 12-15, 1998, 14 pages.
M. Lin et al., "A Transient Liquid Crystal Method Using Hue Angle and a 3-D Inverse Transient Conduction Scheme," ASM Gas Turbines Materials Technology Conference, Oct. 12-15, 1998, 7 pages.
JP1201165 Abstract, Aug. 14, 1989.

* cited by examiner

*Primary Examiner*—Andre J Allen
(74) *Attorney, Agent, or Firm*—Patrick K. Patnode

(57) ABSTRACT

A method of thermal inspection of a part having at least one internal cavity is provided. The method includes flowing a fluid through the at least one internal cavity. The method also includes measuring a temperature at one or more locations on the part over time. The method further includes calculating at least one of a first and a second derivative of the temperature with respect to time. The method also includes comparing at least one of the first or the second derivative to one or more baseline values to determine if the part meets a desired specification.

19 Claims, 5 Drawing Sheets

SYSTEM AND METHOD FOR THERMAL INSPECTION OF PARTS

BACKGROUND

The invention relates generally to thermal inspection systems and methods and more specifically, to non-destructive thermal inspection for internal cavities in a part.

There are several techniques that are currently used for inspection of parts for internal cavities. A commonly used technique is "flow checks". A flow check measures a total flow through a part. Blockage of various film holes or rows of holes, or entire flow circuits or passages, provides measurements for the remaining holes or groups of holes, or flow circuits. The process is repeated with various holes or passages blocked until all desired measurements have been made. Comparisons to either gauge measurements on reliable parts and analytical models of flow circuits determines the acceptability of the parts. However, the technique is known to be time consuming resulting in a check of only selective film holes, groups of holes, or flow circuits. Additionally, the technique has the propensity to overlook local or individual features or holes that are out of specification.

Other techniques include dimensional gauges, for example pin checks, and other visual methods, for example water flow. Industry typically relies on these methods to determine the quality of each part as compared to a nominal standard part or a specification. However, such dimensional or visual techniques do not lend themselves to distinguishing between two parts that may have very different thermal-flow performance, but which flow the same amount and otherwise pass all external dimensional and visual tests.

Pulsed thermography is a surface inspection technique in which a thermal pulse (or flash) is applied to a part, and the thermal response of the surface of part is then detected. However, thermal saturation is not achieved with pulsed thermography due to the limited time duration and penetration of the part. Accordingly, the global thermal conduction response for the part cannot be determined using pulsed thermography, due to the limited thermal penetration depth of that method.

Accordingly, there is a need for an improved method of thermal inspection and specifically, there is a need for a quantitative, non-destructive thermal inspection system and method. In particular, there is a need for a thermal inspection technique that determines the global, thermal response of a part.

BRIEF DESCRIPTION

In accordance with one embodiment of the invention, a method of thermal inspection of a part having at least one internal cavity is provided. The method includes flowing a fluid through the at least one internal cavity. The method also includes measuring a temperature at one or more locations on the part over time. The method further includes calculating at least one of a first and a second derivative of the temperature with respect to time. The method also includes comparing at least one of the first or the second derivative to one or more baseline values to determine if the part meets a desired specification.

In accordance with another embodiment of the invention, a system for thermal inspection of a part having at least one internal cavity is provided. The system includes a fluid source configured to provide a flow of a fluid to the part. The system also includes a camera configured to capture a plurality of images corresponding to a thermal response of the part to the flow. The system further includes a processor configured to calculate at least one of a first and second derivative of a temperature with respect to time and compare at least one of the first or the second derivative to at least one of a baseline value or an acceptable range of values, to determine if the part meets a desired specification.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention are directed to a system and a method for thermal inspection of parts. Example 'parts' include equipment used in engine systems such as, but not limited to, turbine engines. A non-limiting example of the part is a turbine airfoil. The system and method, described below, enable inspection of an internal cavity within the part. The term 'cavity' refers to any type of internal flow area including small diameter channels or large volume spaces including any type of geometry, for example, a serpentine cooling path. A common feature is that the cavity is capable of fluid flow within. Non-limiting examples of the internal cavity include film holes, crossover holes, exit holes, flow channels and combinations thereof. These examples are presented for the purpose of illustration only, and the invention is not limited to any specific type of internal cavity but rather is applicable generally to parts with internal cavities. Further, the term "thermal profile" as used herein refers to a temporal response of the temperature at one or more locations on a surface of the part.

Figure 1:
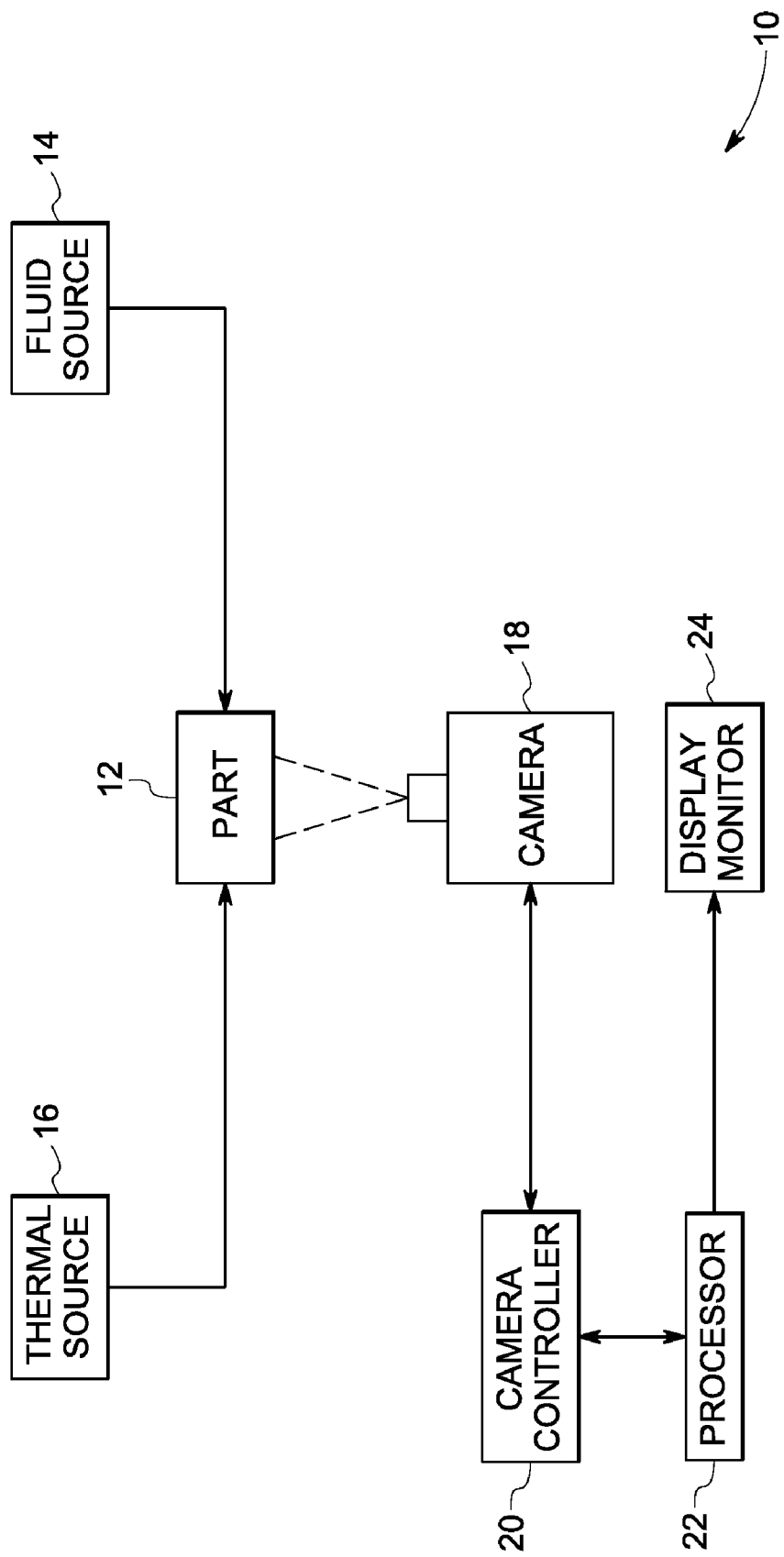
FIG. 1 is a schematic illustration of a thermal inspection system for a part in accordance with embodiments of the invention.

Turning to the drawings, FIG. 1 is a schematic illustration of a thermal inspection system 10 for a part 12. It should be noted that the arrangement shown in FIG. 1 is merely one example of system 10. For example, in certain embodiments, system 10 does not include thermal source 16; instead, either a heating or a cooling fluid is supplied to a part 12, which is initially at room (ambient) temperature. The thermal inspection system 10 includes a fluid source 14 that provides a flow of a fluid to the part 12. A thermal source 16 optionally provides heating or cooling to the part 12. Non-limiting examples of the thermal source 16 include a lamp, an oven, a refrigeration cover and a fluid. In a particular embodiment, the thermal source 16 initially cools the part 12, and the fluid source 14 provides a heating fluid flow to the part 12 to generate a thermal transient within the part 12. In another embodiment, the thermal source 16 initially heats the part 12, and the fluid source 14 provides a cooling fluid flow to the part 12 to generate a thermal transient within the part 12. In yet other embodiments, the part 12 is initially at room temperature, and the fluid source 14 supplies either a cooling or a heating fluid flow to the part 12. In more particular embodiments, the fluid source 14 provides a steady flow of a fluid to the part 12. Non-limiting examples of the fluid include air, nitrogen, steam, water and any Newtonian fluid.

A camera 18 captures a plurality of images of the part 12 at plurality of times, each of the images encompassing a plurality of locations on the part. In an example, the camera 18 is an infrared camera. Each of the images corresponds to the surface temperature of the part 12 at a plurality of locations on the part at a single instance in time in response to the flow of fluid. As used herein, the phrase "response to the flow" refers to a transient test in which a flow is initiated or changed to induce a thermal response. The images are captured in succession over a period of time to obtain a thermal profile of a plurality of surface locations on the part as a function of time. The camera 18 is coupled to a camera controller 20 that controls and automates movement of the camera 18 to capture the images at the successive times. In a particular embodiment, the camera 18 is fixed relative to the part 12. A processor 22 calculates at least one of a first and second derivative of a temperature with respect to time, for each pixel of the images, from the images obtained. Further, the first and the second derivative are compared to one or more baseline values or an acceptable range of values to determine if the part 12 meets a desired specification. Non-limiting examples of the baseline values are one or more local values, mean value of a group of local values and a standard deviation of a group of local values. Moreover, "baseline values" can be extracted, for example, using sample (or "nominal") parts that meet the desired specifications. In the illustrated embodiment, the processor 22 is also coupled to the camera controller 20 and outputs results obtained on a display monitor 24.

It should be noted that the present invention is not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

The processor 22 is typically capable of capturing an image frame rate of adequate frequency, for example greater than 10 frames per second and typically greater than 15 frames per second, from the camera device 18. The temperature-time history of the part 12 is readily measured by the use of the camera 18 and the processor 22. The temperature-time history of each location on an external surface of the part 12 is recorded in the processor 22 for analysis. Detailed measurement of the external surface temperature distribution is dependent on the resolution of the camera 18, i.e. the density of a pixel array in the camera 18. It will be appreciated that in an exemplary embodiment, the part 12 may be coated with temperature indicating coatings in conjunction with an optical detection and a recording system to measure surface temperatures.

As noted above, in certain embodiments, the part 12 is heated or cooled to an initial starting temperature, or temperature distribution, that is measured. In other embodiments, the part 12 resides at room temperature initially. For the former embodiments, at a time t=0, the heating or cooling of the part 12 is stopped, and the temperature of the part 12 is measured and stored in the processor 22. Further, an internal steady flow is introduced from the flow source 14. In exemplary embodiments, the internal steady flow provides heating or cooling. The part 12 is imaged using the camera 18, and associated external surface temperatures are recorded as a function of time in the processor 22. The actuation of the flow can be sudden or gradual, but the flow rate must remain substantially steady during the time period of usable data, thereby providing a "steady-flow thermal transient" during this time period. In a particular embodiment, an initial temperature difference between the part 12 and the flow of the fluid is in the range between 200 F. to about 400 F. In another embodiment, the temperature difference prior to imaging is between about 250 F. to about 350 F.

In one embodiment, if the part 12 is heated to a known temperature, then a cooling transient is initiated by introduction of a cool fluid flow from the fluid source 14 to the part 12. In another embodiment, if the part 12 is cooled to a known temperature, then a heating transient is initiated by introduction of a heated fluid flow to the part 12. In yet another embodiment, a heating or a cooling transient is initiated by introduction of a heated or a cooled fluid respectively into the part 12 that is initially at room temperature.

Figure 2:
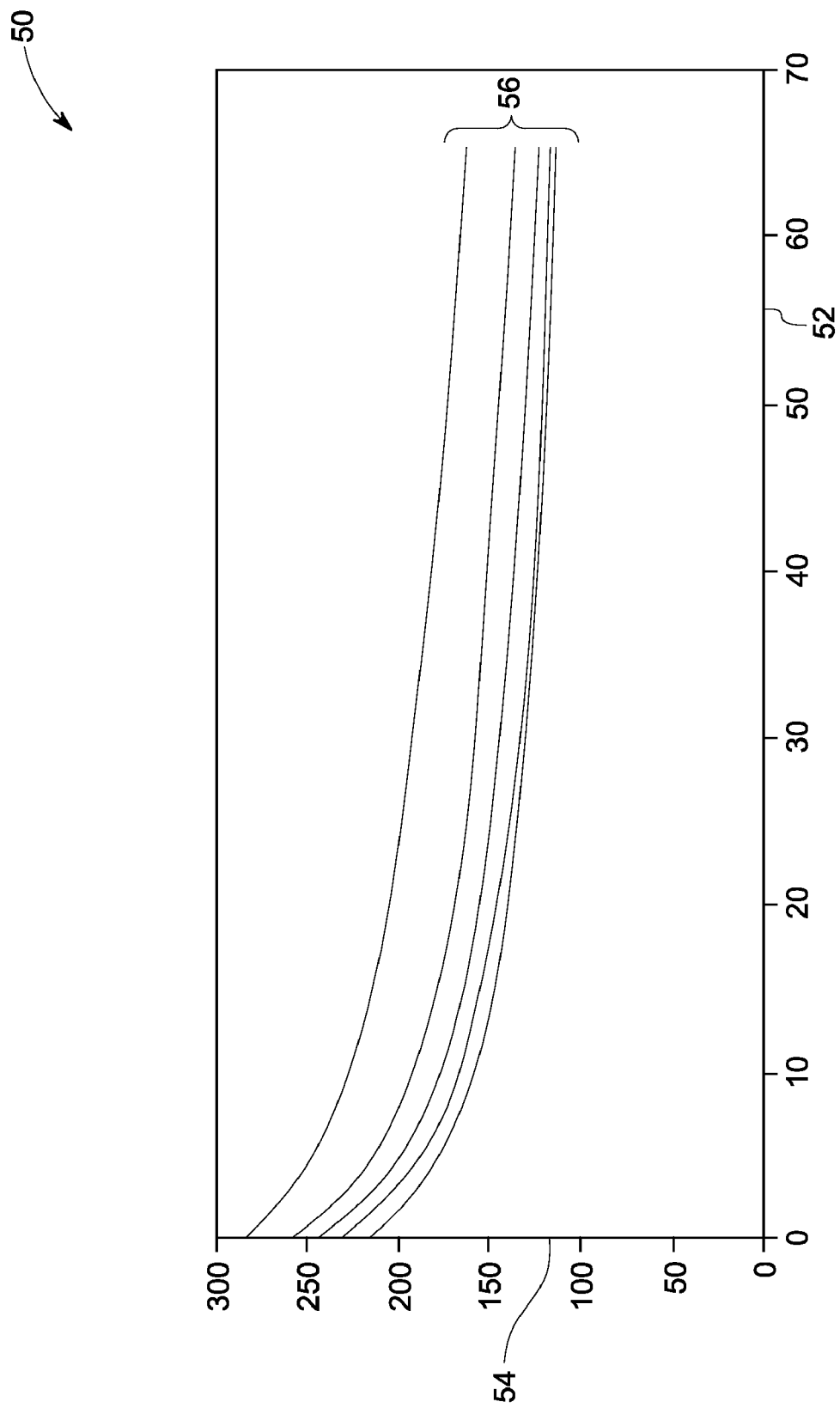
FIG. 2 is a graphical illustration of temperature measured over time at various regions of interest in the part using the inspection system in FIG. 1.

FIG. 2 is a graphical illustration 50 of temperature measured over time at various regions of interest on the part 12 in response to a cooling transient. At an initial time t=0, a thermal transient is initiated by introduction of a cooling fluid into the part 12. The X-axis 52 represents time measured in seconds (s). The Y-axis 54 represents temperature measured in degrees Fahrenheit (° F.). Set of curves 56 represent temperatures measured at various locations on a part. Each of the set of curves 56 represents a specific location on the part 12. The curves 56 indicate a decay in temperature over time. It will be appreciated that all locations on the part 12 need not have similar decay curves as depicted by the curves 56.

Figure 3:
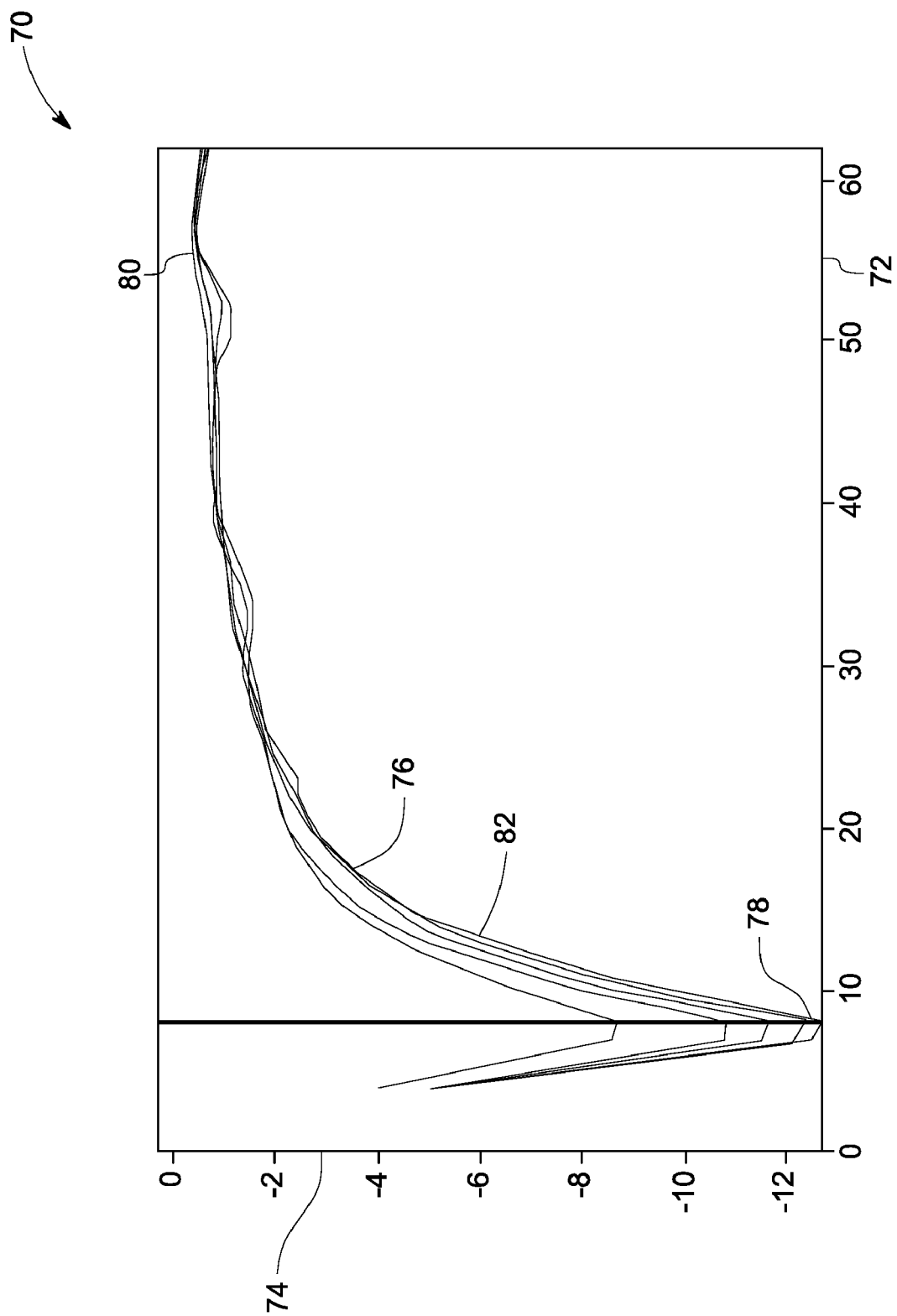
FIG. 3 is a graphical illustration of a calculated first derivative of temperature with respect to time at the various regions of interest.

FIG. 3 is a graphical illustration 70 of a first derivative of temperature with respect to time obtained from FIG. 2. The X-axis 72 represents time in seconds. The Y-axis 74 represents the first derivative of temperature measured in (° F./s). Each of a set of curves 76 represent a first derivative of temperature measured at a specific location over time and correspond to each of the set of curves 56 in FIG. 3. Each of the curves 76 reaches minima 78 and further increases rapidly as indicated by 80 to approach a nearly constant value 82. The nearly constant value 82 is an approach to a value of zero, implying that the location on the part 12 is approaching the same temperature as the fluid. The minima 78 indicates attaining a steady flow of the fluid.

Figure 4:
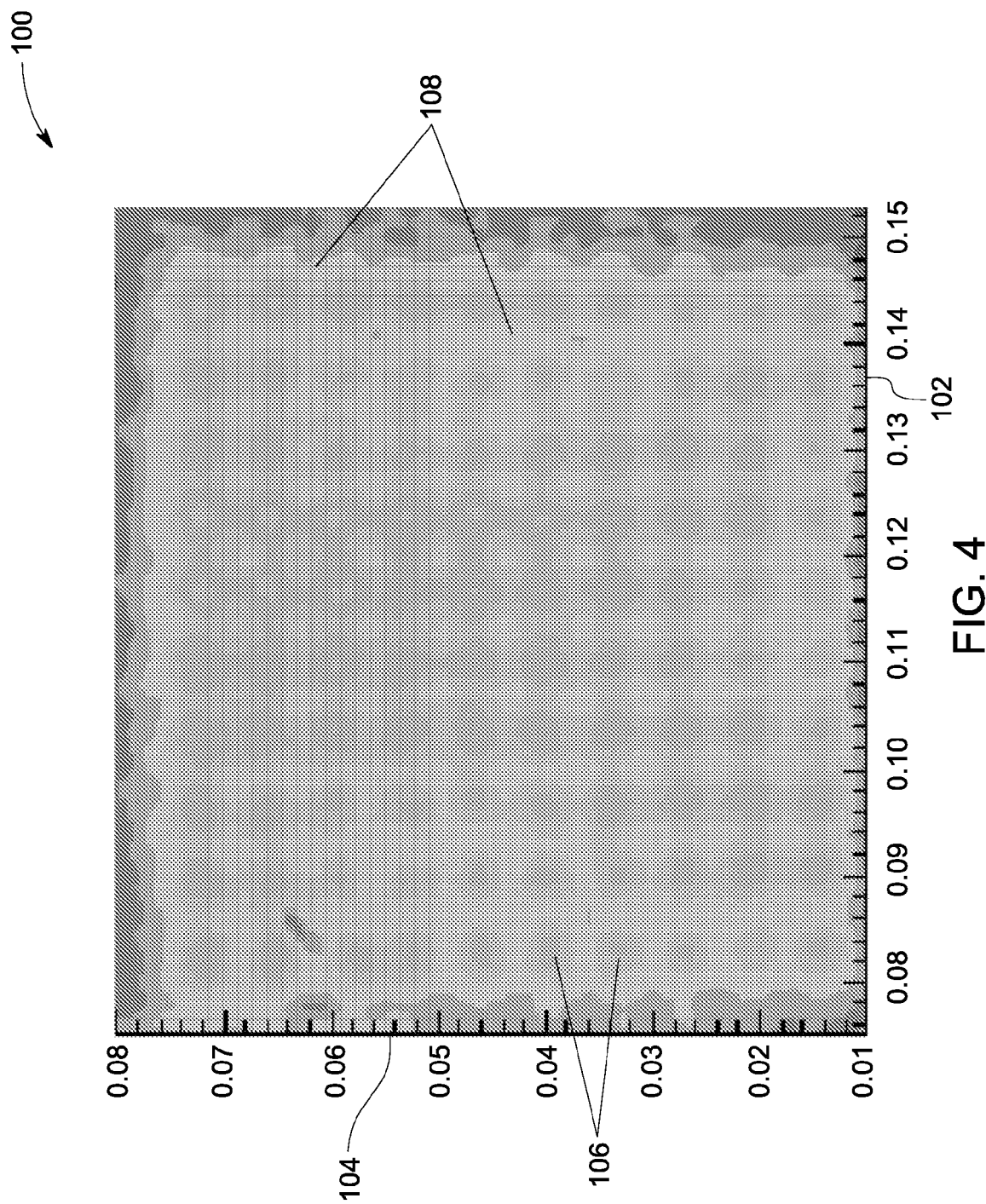
FIG. 4 is a mapping of a surface profile of a region of interest in the part based upon a calculated first derivative of an entire surface of the part.

FIG. 4 is a surface map 100 of an instantaneous first derivative of temperature of the part with respect to time obtained from a data set of an entire surface of the part showing local spatial coordinates as the axes. The X-axis 102 represents distance along a horizontal axis measured in meters. The Y-axis 104 represents distance along a vertical axis measured in meters. A region 106 indicates a thermal response due to internal cooling features such as impingement jet holes and a region 108 indicates a thermal response of a bulk portion of the part adjacent to impingement cooling jets. In addition, a surface map (not shown) can be generated of the second derivative of the temperature of the part with respect to time, $d^2T/dt^2$. The maps can be over the entire surface or over a region of interest on the surface.

Beneficially, the map of the first or second derivative of temperature with time, specifically under the requirement of steady internal flow (including flow through any exit holes), provides an immediate assessment of the thermal adequacy for the complete thermal design of the part as a whole or a specific location on the part. Namely, the map contains the complete conjugate heat transfer of the part. Thus, the map contains all internal cooling and material conduction and thermal diffusivity effects, resulting from internal ribs, film holes, internal bumps, crossover holes, and other features.

Accordingly, the above described technique differs from that described in commonly assigned U.S. Pat. No. 6,804, 622, Bunker et al., "Method and apparatus for non-destructive thermal inspection," in that the present technique does not seek to determine internal heat transfer coefficients. Instead, the present technique is directed to determining the combined thermal response of all thermal influences in the manufactured part. Consequently, the present technique provides a more immediate measure of thermal acceptability or rejection for a cooled part, especially for a complex cooled part, such as a turbine airfoil.

Figure 5:
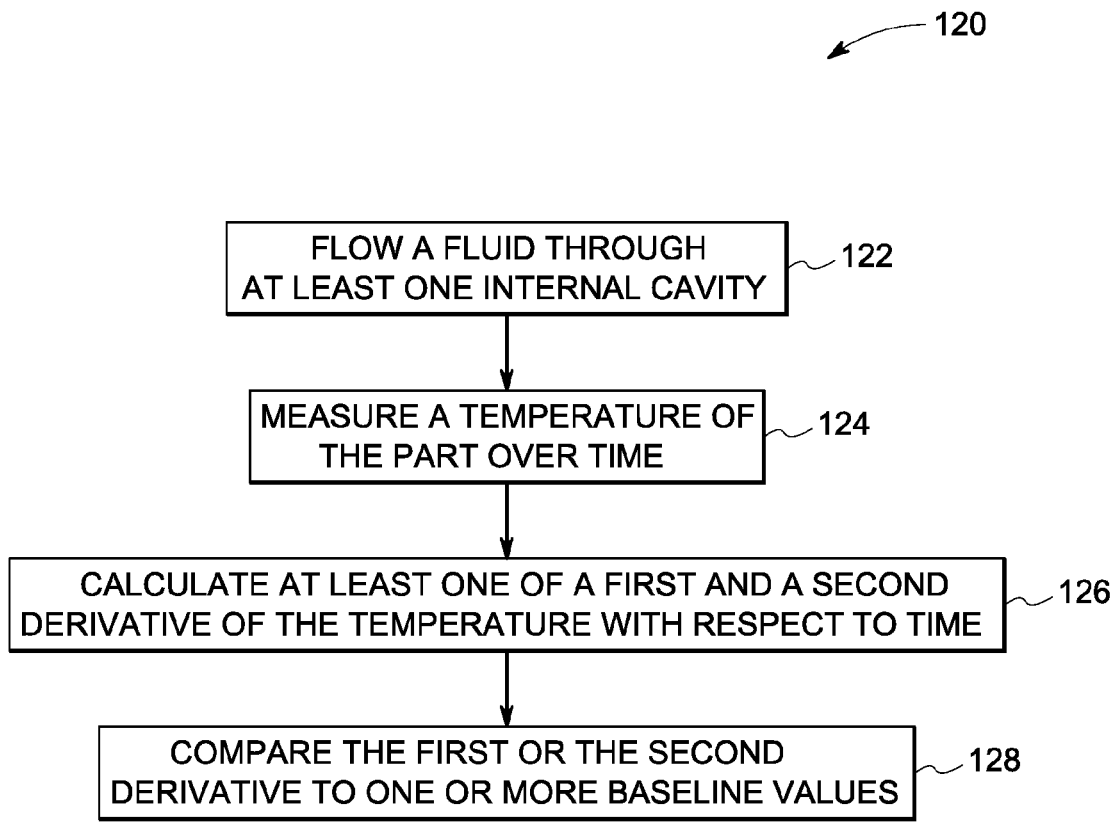
FIG. 5 is a flow chart representing steps in an exemplary method for inspecting an internal cavity in a part in accordance with embodiments of the invention.

FIG. 5 is a flow chart representing steps in an exemplary method 120 for inspecting an internal cavity in a part. The method 120 includes flowing a fluid through the at least one internal cavity in step 122 to provide a steady-flow thermal transient. In particular embodiments, step 122 is performed after initially heating or cooling the part. In other embodiments, step 122 is performed for a part 12 that is initially at room (ambient) temperature. In particular embodiments, a steady flow of the fluid is introduced. In an example, a steady flow of a cooling fluid is introduced. In another example, a steady flow of a heating fluid is introduced. In another embodiment, the steady-flow thermal transient is generated in a part initially at room temperature. Surface temperature is measured over time at various regions of interest on the part in step 124. In an exemplary embodiment, the temperature is measured via an infrared camera. A surface profile of the part is mapped using the measured temperature. Further, at least one of a first and a second derivative of the temperature with respect to time is calculated in step 126. The first derivative and/or the second derivative is compared to one or more baseline values to determine if the part meets a desired specification in step 128. In one embodiment, the first derivative and the second derivative are compared to upper and lower specification limits for the part. For parts that fail to meet the specifications, the part can either be rejected or subjected to rework.

The above described inspection process can be performed at a variety of manufacturing stages. For example, the inspection can be performed at the initial manufacturing stage and could also be used on parts that have gone through a repair process. In addition, the inspection could be performed for parts prior to repair to determine whether repair is needed. For turbine parts, the inspection could be performed after investment casting and prior to final machining. The inspection could also be performed after final machining. Further, the inspection could be performed after film holes were formed (post-casting process) and before or after coatings are applied.

The various embodiments of a system and method for thermal inspection of parts described above thus provide a way to measure a raw and combined thermal response of all thermal influences in a part. These techniques and systems also allow for highly accurate thermal inspection due to the ability to penetrate to desirable depths in the part. It is important to note that while detailed internal heat transfer coefficients, such as those presented in U.S. Pat. No. 6,804,622, are very desirable as verification of the design boundary conditions for the part, the total thermal response is closer to the engine operational needs. Thus, the present technique provides a faster and more relevant measure of acceptance in inspections. Unlike the internal heat transfer coefficient approach of U.S. Pat. No. 6,804,622, additional finite element modeling (FEM) analyses are not required for the present technique. The dimensionality of the part (for example, rib and wall thickness) will automatically be accounted using the present method.

Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of an example of a camera described with respect to one embodiment can be adapted for use in a system used to measure temperatures calculating a second derivative of temperature described with respect to another. Similarly, the various features described, as well as other known equivalents for each feature, can be mixed and matched by one of ordinary skill in this art to construct additional systems and techniques in accordance with principles of this disclosure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of thermal inspection of a part having at least one internal cavity, the method comprising:
flowing a fluid through the at least one internal cavity;
measuring a temperature at one or more locations on the part over time;
calculating at least one of a first and a second derivative of the temperature with respect to time; and
comparing at least one of the first or the second derivative to one or more baseline values to determine if the part meets a desired specification.

2. The method of claim 1, further comprising heating or cooling the part prior to performing the flowing step, wherein flowing the fluid provides a steady-flow thermal transient.

3. The method of claim 1, wherein the part is at room temperature prior to performing the flowing step.

4. The method of claim 1, wherein the flowing comprises introducing a steady flow of the fluid.

5. The method of claim 4, wherein the fluid comprises a cooling fluid.

6. The method of claim 4, wherein the fluid comprises a healing fluid.

7. The method of claim 1, wherein the measuring comprises measuring the temperature at the one or more locations on the part via an infrared camera.

8. The method of claim 1, further comprising mapping a thermal profile of the part prior to performing the calculating step.

9. The method of claim 1, wherein the comparing comprises comparing at least one of the first or the second derivative to an upper and a lower specification limit of the part.

10. A system for thermal inspection of a part having at least one internal cavity, the system comprising:

a fluid source configured to provide a flow of a fluid to the part, a camera configured to capture a plurality of images corresponding to a thermal response of the part to the flow, and a processor configured to:
   calculate at least one of a first and second derivative of a temperature with respect to time; and
   compare at least one of the first or the second derivative to one or more baseline values or an acceptable range of values to determine if the part meets a desired specification.

11. The system of claim 10, further comprising a thermal source configured to heat or cool the part.

12. The system of claim 11, wherein the thermal source comprises one of a lamp, an oven, and a fluid.

13. The system of claim 12, wherein the fluid comprises a cooling or a heating fluid.

14. The system of claim 13, wherein the cooling fluid comprises one of air, nitrogen, steam, water, or a Newtonian fluid.

15. The system of claim 13, wherein the heating fluid comprises one of air, nitrogen, steam, water, or a Newtonian fluid.

16. The system of claim 10, wherein the internal cavity is selected from the group consisting of film holes, crossover holes, exit holes, flow channels and combinations thereof.

17. The system of claim 10, further comprising a camera controller configured to control the camera to measure temperature of the part over time.

18. The system of claim 10, wherein the camera comprises an infrared camera.

19. The system of claim 10, wherein the flow of the fluid comprises a steady flow.

* * * * *

UNITED STATES PATENT AND TRADEMARK OFFICE
CERTIFICATE OF CORRECTION

PATENT NO. : 7,651,261 B2
APPLICATION NO. : 11/775502
DATED : January 26, 2010
INVENTOR(S) : Bunker et al.

It is certified that error appears in the above-identified patent and that said Letters Patent is hereby corrected as shown below:

On the Face Page, in Field (56), under "OTHER PUBLICATIONS", in Column 2, Line 1, delete "Infared" and insert -- Infrared --, therefor.

In Column 6, Line 56, in Claim 6, delete "healing" and insert -- heating --, therefor.

Signed and Sealed this

Twenty-third Day of November, 2010

David J. Kappos
*Director of the United States Patent and Trademark Office*